United States Patent
Duqi et al.

(10) Patent No.: US 11,603,311 B2
(45) Date of Patent: Mar. 14, 2023

(54) WATERPROOF SWITCH ACTUATABLE BY A FLUID SUCH AS AIR AND USABLE IN PARTICULAR FOR ACTIVATING AN INHALATOR APPARATUS, SUCH AS AN ELECTRONIC CIGARETTE

(71) Applicant: STMicroelectronics S.r.l., Agrate Brianza (IT)

(72) Inventors: Enri Duqi, Milan (IT); Fabrizio Cerini, Magenta (IT); Lorenzo Baldo, Bareggio (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 328 days.

(21) Appl. No.: 17/072,813

(22) Filed: Oct. 16, 2020

(65) Prior Publication Data
US 2021/0114867 A1   Apr. 22, 2021

(30) Foreign Application Priority Data
Oct. 17, 2019   (IT) .......................... 102019000019169

(51) Int. Cl.
*B81B 7/02* (2006.01)
*A24F 40/51* (2020.01)
*B81B 7/00* (2006.01)

(52) U.S. Cl.
CPC ............... *B81B 7/02* (2013.01); *A24F 40/51* (2020.01); *B81B 7/0009* (2013.01); *B81B 2201/0264* (2013.01); *B81B 2203/0127* (2013.01)

(58) Field of Classification Search
CPC . B81B 7/02; B81B 7/0009; B81B 2201/0264; B81B 2203/0127; A24F 40/51;
(Continued)

(56) References Cited

U.S. PATENT DOCUMENTS 10,334,887 B1   7/2019   Qiu
2005/0087020 A1*   4/2005   Ueyanagi ............ G01L 19/0038
73/753
(Continued)

FOREIGN PATENT DOCUMENTS

| EP | 3 196 952 A1 | 7/2017 |
| EP | 3 205 997 A1 | 8/2017 |
| EP | 3 330 688 A1 | 6/2018 |

*Primary Examiner* — Yasser A Abdelaziez
(74) *Attorney, Agent, or Firm* — Seed Intellectual Property Law Group LLP

(57) ABSTRACT

A MEMS switch is actuatable by a fluid, and includes a piezoelectric pressure sensor that detects the movement of a fluid generating a negative pressure. The piezoelectric pressure sensor is formed by a chip of semiconductor material having a through cavity and a sensitive membrane, which extends over the through cavity and has a first and a second surface. The piezoelectric pressure sensor is mounted on a face of a board having a through hole so that the through cavity overlies and is in fluid connection with the through hole. The board has a fixing structure, which enables securing in an opening of a partition wall separating a first and a second space from each other. The board is arranged so that the first surface of the sensitive membrane faces the first space, and the second surface of the sensitive membrane faces the second space.

20 Claims, 4 Drawing Sheets

(58) Field of Classification Search
CPC . G01L 19/0092; G01L 9/008; H01L 41/1132; A61B 5/4818; A61B 2562/0247; A61M 15/002; A61M 15/0021; A61M 2016/0021; A61M 2016/0024; A61M 2016/0027; A61M 2202/0468; A61M 2205/0238; A61M 2205/0294; A61M 2205/332; A61M 2205/3331; A61M 2205/3358; A61M 2205/3653; A61M 2205/50; A61M 2205/583; A61M 2205/8206; A61M 11/042; A61M 15/06
See application file for complete search history.

(56) References Cited

U.S. PATENT DOCUMENTS

| | | |
|---|---|---|
| 2005/0218488 A1 | 10/2005 | Matsuo |
| 2006/0139393 A1* | 6/2006 | Zhang ............... B41J 2/17566 347/19 |
| 2014/0069432 A1* | 3/2014 | Mebasser ........... F04D 25/0613 128/205.25 |
| 2016/0128389 A1 | 5/2016 | Lamb et al. |
| 2017/0230758 A1 | 8/2017 | Kuntzman et al. |
| 2018/0136063 A1 | 5/2018 | Wagner |
| 2018/0317022 A1 | 11/2018 | Evans et al. |
| 2019/0200675 A1 | 7/2019 | Bache et al. |
| 2019/0350260 A1* | 11/2019 | Di Marco ............ A61M 15/06 |

* cited by examiner

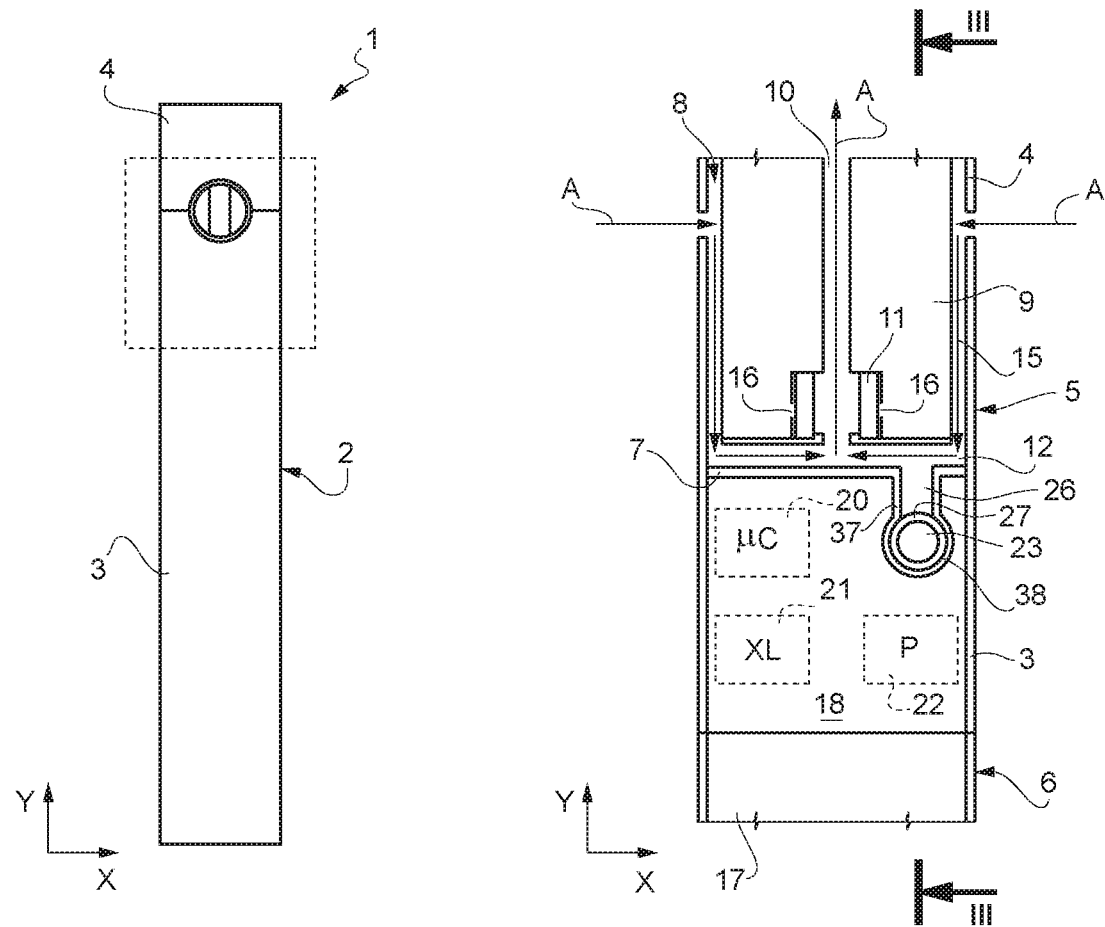
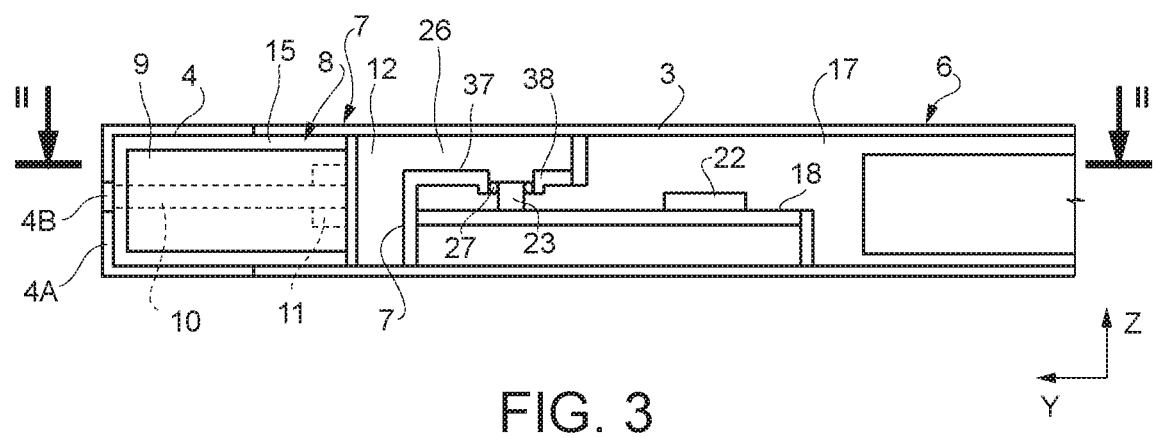
FIG. 1 (Prior Art)
FIG. 2 (Prior Art)
FIG. 3 (Prior Art)

WATERPROOF SWITCH ACTUATABLE BY A FLUID SUCH AS AIR AND USABLE IN PARTICULAR FOR ACTIVATING AN INHALATOR APPARATUS, SUCH AS AN ELECTRONIC CIGARETTE

BACKGROUND

Technical Field

The present disclosure relates to a waterproof switch actuatable by a fluid such as air and usable in particular for activating an inhalator apparatus, such as an electronic cigarette.

Description of the Related Art

In particular, in the following description, reference will be made to an on/off switch used in an electronic cigarette, but the switch may find advantageous application also in inhalators of different types, for example in Continuous Positive Airway Pressure (CPAP) devices, used for sleep-apnea detection, in anti-pollution masks, in apparatus for detecting leakages of air or other fluids, employed in the industrial field, and in general in the automotive sector.

As is known, inhalators are apparatus that enable inhalation of a fluid (for example, air containing nicotine, air, or an aerosol containing medicaments or other substances, for medical or veterinary use) using the respiratory system of a living being.

In these devices, in particular in case of discontinuous use, generally a separate on/off device is provided. For instance, in an electronic cigarette, an always active accelerometer is generally present that waits for a characteristic signal (for example, a sequence of tapping with fingers, so-called tap-tap) for waking up the rest of the components. In particular, when the accelerometer recognizes the finger tapping sequence by the user, it generates an activation signal for a circuit that controls vaporization of a suitable liquid solution, contained in the electronic cigarette, without combustion of substances.

To this end, the electronic cigarette comprises a vaporization chamber, or atomizer, containing a resistance, for example shaped as a winding (and therefore generally referred to as coil), which, when powered by a battery, directly or indirectly heats the liquid solution, causing it to evaporate.

To activate the coil, commercially available electronic cigarettes may comprise a local pressure sensor, which measures the pressure within the vaporization chamber, an environmental pressure sensor (barometer), which measures the pressure of the external environment, and a circuit that compares the signals generated by the sensors, to determine when the user is inhaling air.

Moreover, the electronic cigarette is frequently provided with an light indicator, such as an LED, which signals when the cigarette is ready to function and may be provided with an end piece that lights up when inhaling is detected, thus simulating the typical red color of a traditional cigarette combustion, so as to reproduce the sensation, also optical, of traditional cigarette smoking.

An example of circuits for activating an electronic cigarette of the indicated type is illustrated in FIGS. 1-3.

In detail, FIGS. 1-3 show an electronic cigarette 1 having a housing 2 with a larger dimension (length) along a first axis Y of a Cartesian coordinate system XYZ and cross-section area (in planes parallel to the Cartesian plane XZ) smaller than the length. The housing 2 comprises a tubular portion 3 and an inhalation portion 4 arranged as a prosecution of each other along the first axis Y and having here the same cross-section, for example circular, rectangular or ovalised.

The inhalation portion 4 is open at a first end, facing the tubular portion 3, and has a second end closed by an end wall 4A (FIG. 3) provided with an inhalation opening 4B, shown with a dashed line in FIG. 3, to enable inhalation by a smoker.

The tubular portion 3 is open at both ends and is divided internally into a first and a second part 5, 6 by a partition wall 7, which extends transversely to the tubular portion 3 (generally parallel to the Cartesian plane XZ).

The first part 5 of the tubular portion 3 is arranged in proximity of the inhalation portion 4 and forms therewith a vaporization chamber 8 accommodating a tank 9, an air channel 10, surrounded by the tank 9, and a heater 11, arranged between the tank 9 and the air channel 10 near the partition wall 7. A first gap 12 extends between the partition wall 7 and the bottom of the tank 9, throughout the cross area of the tubular portion 3, and is in fluid connection with the air channel 10. A second gap 15, of a tubular shape, is arranged between the wall of the first part 5 of the tubular portion 3 and the tank 9, is in fluid connection with the first gap 12 and opens outwards at the mutually facing ends of the tubular portion 3 and of the inhalation portion 4. The second gap 15, the first gap 12, and the air channel 10 form a fluid path (indicated by arrows A) for the air inhaled through the inhalation opening 4B in the end wall 4A of the inhalation portion 4.

The air channel 10 and the tank 9 are in connection through one or more holes 16 that allow a fluid in the tank 9 to percolate towards the heater 11, where it is vaporized and mixed with the air inhaled. A spongy region or a fabric, not illustrated, may be arranged in proximity of the heater 11, to facilitate liquid to exit the tank 9 and vaporize. In a variant not shown, the air channel 10 is not a channel physically separate from the tank 9, but the tank 9 has holes at the bottom facing the first gap 12 to enable the passage of the air through the tank 9, mixing with the vaporized substances, to create a virtual channel.

The second part 5 of the tubular portion 3 forms an open chamber 17 housing a board 18 arranged longitudinally with respect to the housing 2 and carrying electronic components 20-23, as specified below.

In particular, the electronic components 20-23 comprise a control unit 20, for example an ASIC or a microcontroller, an accelerometer 21, an environmental pressure sensor 22, and an internal pressure sensor 23. The second part 5 of the tubular portion 3 further accommodates a battery 24, shown schematically and electrically coupled to the electronic components 20-23 in a way not shown, for their electrical power supply.

The control unit 20 is moreover electrically coupled to all the other electronic components 21-23 and to the heater 11, in a way not shown, so as to receive the detected movement and pressure signals and control the operation of the heater 11, as explained hereinafter.

The environmental pressure sensor 22 is sensitive to the pressure existing in the open chamber 17, and thus measures the pressure in the external environment. The internal pressure sensor 23 faces a detection channel 26 delimited by a channel wall 37 extending from the partition wall 7 towards the inside of the second part 6 of the tubular portion 3. The channel wall 37 has an opening, from which a portion of tubular wall 38 extends towards the board and surrounds the internal pressure sensor 23. A seal gasket 27 is arranged between the internal pressure sensor 23 and the portion of tubular wall 38, sealing the fluid path of the inhaled air and the sensitive part of the internal pressure sensor 23 from the open chamber 17. Moreover, a gel mass covers the internal pressure sensor 23 to allow the latter to detect the pressure in the first gap 12 and protect it from any possible leakages of liquid exiting the tank 9.

The electronic cigarette 1 operates as follows.

The accelerometer 21 is always on and remains waiting to recognize the activation sequence by the user, for example a succession of taps on the electronic cigarette 1.

Upon detecting the taps, the accelerometer 21 sends the corresponding signals to the control unit 20, which, upon recognition of the specific activation sequence, switches on the other components, in particular the environmental pressure sensor 22 and the internal pressure sensor 23. If envisaged, the control unit 20 switches on an LED for signaling that the electronic cigarette 1 is ready.

When the user starts to inhale through the inhalation opening 4B at the end wall of the inhalation portion 4, air is inhaled from outside along the path indicated by the arrows A, entering the inlet opening between the tubular portion 3 and the inhalation portion 4, and traveling along the fluid path formed by the second gap 15, the first gap 12, and by the air channel 10. In the detection channel 26 a negative pressure is thus created. The internal pressure sensor 23 facing the detection channel 26 detects the negative pressure and generates a corresponding signal for the control unit 20. The control unit 20 recognizes the inhalation and activates the heater 11 on the basis of the difference of the signals of the internal pressure sensor 23 and of the environmental pressure sensor 22. Consequently, the control unit 20 heats the liquid coming from the tank 9 (possibly soaking into the spongy region or the fabric, not shown) and vaporizes it, causing mixing thereof with the inhaled air.

This operating scheme is somewhat complex and involves high power consumptions, both because of the high number of components and of the accelerometer 21 always being on. Moreover, it has non-negligible costs.

U.S. Pat. No. 10,334,887 describes an atomizer provided with a single sensor that is arranged along the fluid path of the inhaled air and is able to detect the negative pressure generated by inhaling. Upon detection of the negative pressure, the sensor (formed by a strain gauge, of a resistive or capacitive type) generates a trigger signal, sent to a controller controlling the power supply to a heater.

This solution partially solves the problem of cost referred to above, since it uses just one sensor, but not the problem of consumption, since the sensor has to be always on and powered, to detect the pressure existing in the fluid path.

BRIEF SUMMARY

The aim of the present disclosure is therefore to provide a device that overcomes the drawbacks of the prior art.

According to the present disclosure a MEMS switch actuatable by a fluid is provided, as defined in the attached claims.

BRIEF DESCRIPTION OF THE SEVERAL VIEWS OF THE DRAWINGS

For a better understanding of the present disclosure, embodiments thereof are now described, purely by way of non-limiting example, with reference to the attached drawings, wherein:

FIG. 1 is a side view of a known electronic cigarette;

FIG. 2 is a cross-section, taken along section line II-II of FIG. 3, of a part of the electronic cigarette of FIG. 1;

FIG. 3 is a longitudinal section, taken along section line of FIG. 2, of the electronic cigarette of FIG. 1;

DETAILED DESCRIPTION

Figure 4:
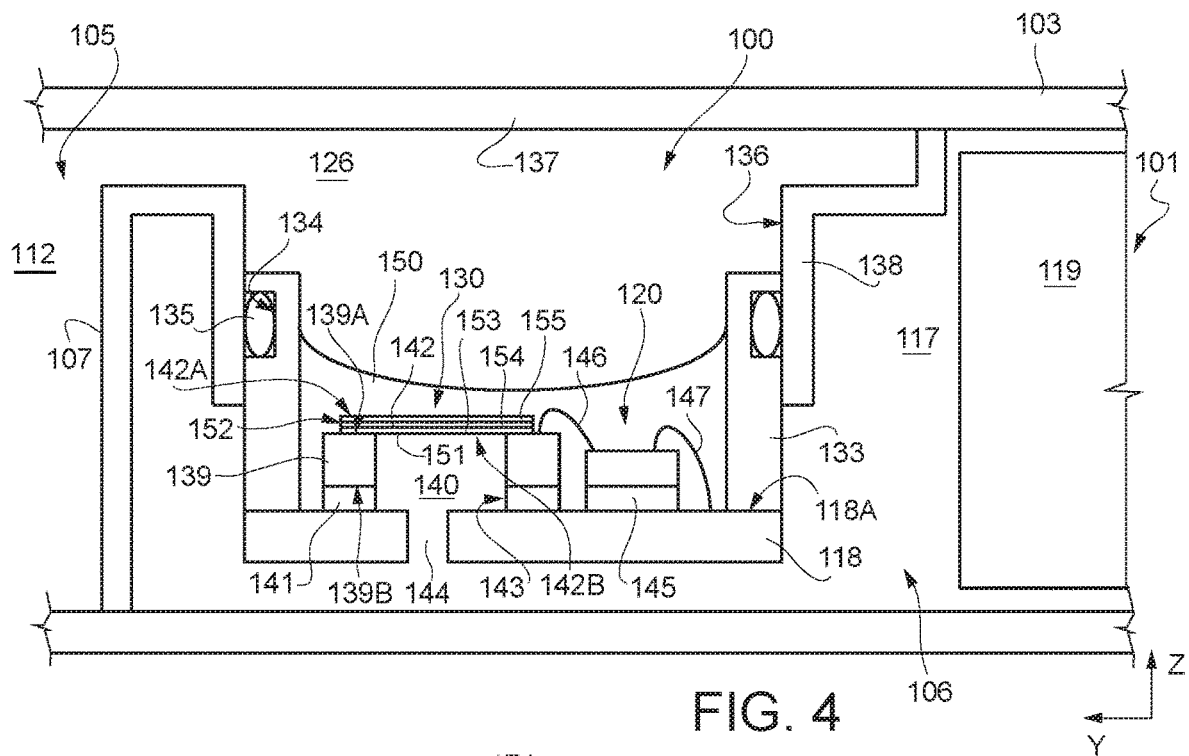
FIG. 4 is a cross-section of a portion of a cigarette including the present switch according to one embodiment.

FIG. 4 shows a portion of an electronic cigarette 101 having the general structure illustrated in FIGS. 1-3 and including a switch according to the present disclosure. Consequently, the general structure of the electronic cigarette is not reproduced in the drawings, and the parts of the electronic cigarette similar to those described with reference to FIGS. 1 and 3 are designated by reference numbers increased by 100.

Also here, the electronic cigarette 101 has an elongated shape in a direction parallel to a first axis Y of a Cartesian coordinates system XYZ and comprises an inhalation portion (not illustrated) similar to the inhalation portion 4 of FIG. 1 and a tubular portion 103, accommodating a switch 100. In particular, FIG. 4 shows part of the tubular portion 103.

As in FIGS. 1-3, a partition wall 107 extends transversely to the tubular portion 103 and internally divides the latter into a first part 105 and into a second part 106.

Similarly to FIGS. 2 and 3, the first part 105 of the tubular portion 103 is designed to accommodate a tank, an air channel, a heater (not illustrated in FIG. 4, similar to the corresponding components of FIGS. 2-3) and forms a gap 112, similar to the first gap 12 of FIGS. 2-3, and the second part 106 forms an open chamber 117 and accommodates a detection channel 126. The open chamber 117 is designed to accommodate a battery 119 and the switch 100, the latter facing the detection channel 126.

In the embodiment illustrated, the switch 100 comprises a board 118 extending parallel to the longitudinal direction of the electronic cigarette 103 (parallel to a plane YZ of the Cartesian coordinates system XYZ) and carries, on a face 118A thereof, a piezoelectric pressure sensor 130 and a control unit 120.

A channel wall 137 extends from the partition wall 107 towards the inside of the second part 106 of the tubular portion 103 and delimits a detection channel 126. The channel wall 137 has an opening 136 facing the board 118. A tubular wall 138 extends from the opening 136 towards the board 118 and is fixed to the latter via a supporting wall 133.

In the embodiment of FIG. 4, the supporting wall 133 has a generally tubular shape, with a cross-section that is, for example, circular, oval, or polygonal, surrounds the piezoelectric pressure sensor 130, and the control unit 120, and delimits an area approximately equal to the area of the board 118. The supporting wall 133 is fixed at a first end thereof to the face 118A of the board 118 and is partially inserted, at a second end thereof, in the tubular wall 138. In the embodiment illustrated, in proximity of its second end, the supporting wall 133 has a groove 134 which extends peripherally and externally to the supporting wall 133 and accommodates a seal gasket 135. In this way, the sealing of the open chamber 117 with respect to the detection channel 126 is ensured.

The illustrated arrangement is, however, purely exemplary, and the supporting wall 133 can be fixed to the tubular wall 138 or directly to the opening 136 through other retention solutions, for example by snap action, with differently arranged gasket elements.

The piezoelectric pressure sensor 130 is manufactured using the MEMS technique and comprises a chip 139 of semiconductor material, such as silicon, having a top surface 139A on which a membrane 142 is fixed, and a bottom surface 139B fixed to the board 118 through a glue layer 141. The chip 139 has a cavity 140 extending throughout its entire thickness. The glue layer 141 has a first opening 143 at the cavity 140 and aligned thereto. The membrane 142 is suspended over the cavity 140 and has a first face 142A looking toward the detection channel 126 and a second face 142B looking toward the cavity 140. The cavity 140 of the piezoelectric pressure sensor 130 faces a second opening 144 of the board 118, also a through opening, so that the cavity 140 is in fluid connection with the open chamber 117.

The control unit 120 is arranged alongside the piezoelectric pressure sensor 130, is bonded to the board 118 on its face 118A through a glue layer 145 and is formed by an ASIC (Application Specific Integrated Circuit); it is connected to the piezoelectric pressure sensor 130 through first wires 146 and to conductive regions (not illustrated) of the board 118 through second wires 147.

The board 118 may be formed by a standard printed circuit board, of electrically insulating material and comprising conductive regions (not shown) for electrical connection to the control unit 120 (as indicated above), to the battery 119, and to the heater (not shown), in a way known and not shown.

The board 118 is covered, on its face 118A, by a gel mass 150, which also surrounds the piezoelectric pressure sensor 130 and the control unit 120, preventing any drops of liquid, vaporized by the electronic cigarette 101, from coming into contact with the electronic components and damaging them. The gel mass 150 has a higher flexibility than the membrane 142, but is incompressible, so as to transfer the pressure existing in the detection channel 126, and therefore in the gap 112, to the membrane 142.

Consequently, the membrane 142 is subject to the pressure existing in the detection channel 126 on its first face 142A and to the environmental pressure on its second face 142B.

The membrane 142 (see also FIG. 4A) is basically formed by a supporting layer 151, for example of epitaxially grown polycrystalline silicon, and by a piezoelectric stack 152 arranged over the supporting layer 151.

The piezoelectric stack 152 comprises a core region 156, of insulating material, for example aluminum nitride (AlN), a bottom electrode region 153, for example of molybdenum (Mo), a piezoelectric region 154, for example of aluminum nitride (AlN), and a top electrode region 155, for example of molybdenum (Mo).

A passivation layer 171, for example of aluminum nitride (AlN), covers the top electrode region 155 and, laterally, the piezoelectric stack 152, except where the electrical connections are to be provided, as discussed below with reference to FIG. 9.

Figure 4A:
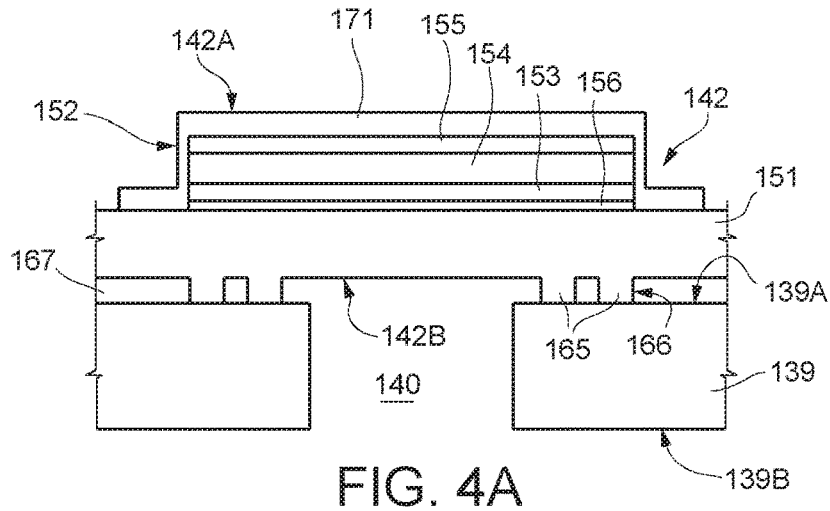
FIG. 4A shows an enlarged detail of FIG. 4.

FIG. 4A moreover shows a possible electrical connection between the supporting layer 151 and the chip 139 through polycrystalline silicon vias 165 extending from the supporting layer 151 through connection openings 166 formed in an oxide layer 167 that covers the top surface 139A of the chip 139.

In FIG. 4A, the chip 139 may have a thickness comprised between 50 and 5000 µm, for example 1000 µm, the oxide layer 167 may have a thickness comprised between 20 nm and 1 µm, for example 500 nm; the supporting layer 151 may have a thickness comprised between 2 and 20, for example 10 µm; the core region 156 may have a thickness comprised between 4 and 50 nm, for example 35 nm; the bottom electrode 153 may have a thickness comprised between 50 and 200 nm, for example 100 nm; the piezoelectric region 154 may have a thickness comprised between 0.1 and 5 µm, for example 1 µm; the top electrode 155 may have a thickness comprised between 50 and 500 nm, for example 100 nm; and the passivation layer 171 may have a thickness comprised between 50 and 1000 nm, for example 100 nm.

In use, when the electronic cigarette 101 is inactive, it absorbs an extremely low current, since only a small input portion of the control unit 120 is on, the heater (not shown) is off, and the piezoelectric pressure sensor 130 is not powered. Furthermore, in this situation, the pressure on the two faces 142A and 142B of the membrane 142 is approximately the same, and the piezoelectric stack 152 is in a resting, unstressed position and does not generate any electrical signal. When a smoker inhales, causing a flow of air according to the arrows A of FIG. 2, a negative pressure is created in the detection channel 126. Consequently, a difference of pressure is set up between the two faces 142A and 142B of the membrane 142 and causes a deformation of the membrane 142 and generation of electrical charge, i.e., of a current, by the piezoelectric region 154. This current is supplied to the control unit 120. When the latter receives the current from the piezoelectric pressure sensor 130, it switches on and activates the heater (not shown), enabling the operation of the electronic cigarette 101.

Thereby, the switch 100, having a single, piezoelectric sensor and exploiting the capacity of piezoelectric materials to generate current when deformed, without any need to be electrically supplied, enables switching on of the cigarette, which starts to absorb current from the battery 119 substantially only upon detecting inhaling by a user.

Figure 5:
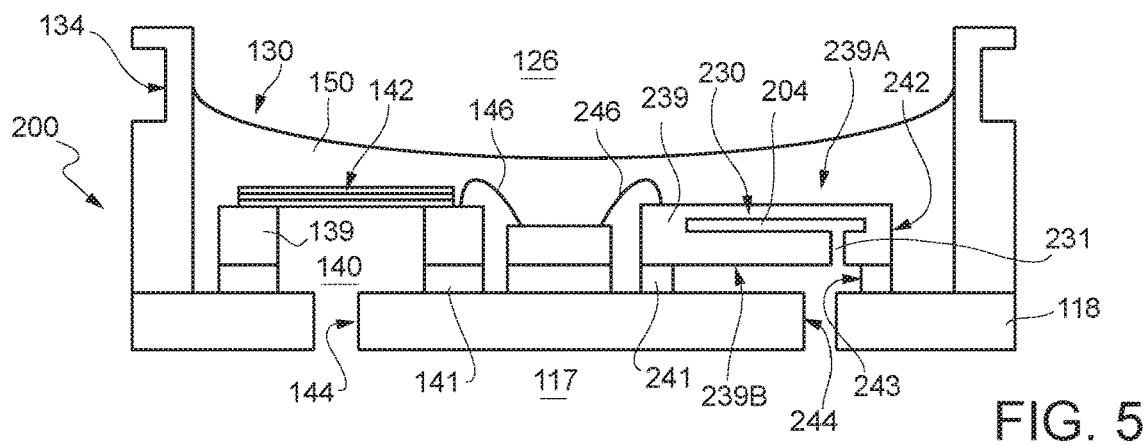
FIG. 5 is a cross-section of a portion of a cigarette including the present switch according to another embodiment.

FIG. 5 shows a switch 200 that also allows a precise measure of the negative pressure existing in the detection chamber 126.

As for the switch 100 of FIG. 4, the switch 200 comprises a board carrying a piezoelectric pressure sensor and a control unit, which are therefore again designated by the reference numbers 130 and 120, respectively. In addition, the switch 200 of FIG. 5 comprises a barometric sensor 230, arranged on the board 118 and also manufactured using MEMS technology.

To facilitate understanding, in the switch 200 of FIG. 5, the chip 139, the membrane 142, the cavity 140 and the glue layer 141 of the piezoelectric pressure sensor 130 will be referred to hereinafter as first chip 139, first membrane 142, first cavity 140 and first glue layer 141.

The barometric sensor 230 may be manufactured in any way suitable to precisely detect differential pressures. For instance, it may be of a capacitive type, of a piezoresistive type, a strain gauge, etc.

The barometric sensor 230 comprises a second chip 239, for example, of semiconductor material such as silicon, having a top surface 239A and a bottom surface 239B. The second chip 239 is fixed to the board 118 at its bottom surface 239B via a second glue layer 241 and has a second cavity 204, which extends underneath and parallel to the top surface 239A of the second chip 239. The portion of the second chip 239 arranged between the top surface 239A and the second cavity 204 forms a second membrane 242. The second cavity 204 is of a buried type and is connected to a third opening 243 in the second glue layer 241 and to a fourth opening 244 in the board 118 through a hole 231 that extends from the bottom surface 239B of the second chip 239 as far as the second cavity 204. The hole 231 has a diameter much smaller than the second cavity 204.

Furthermore, the second chip 239 is connected to the control unit 120 through third wires 246 and is also surrounded by the gel mass 150.

The barometric sensor 230 has a high precision in detecting the differential pressure existing between the detection chamber 126 and the open chamber 117 and outputs a precise differential pressure signal, which is supplied to the control unit 120 of the switch 200. This precise signal may therefore be used by the control unit 120 of the switch 200 for outputting precise flow information and in case controlling further components for adjustment purposes. The barometric sensor 200, which has a non-negligible current consumption, may here be activated by the control unit 120 only after the piezoelectric sensor 130 has activated the latter, thus limiting its consumption only after the piezoelectric switch 130 has detected inhaling or, in general, the presence of a flow of air such as to cause a deformation of the membrane 142.

The above solution is particularly advantageous when the switch 200 is used in an inhalation apparatus of a medical type or in a sensor for detecting pressure losses in an industrial environment, where it is desired that the switch, in addition to activating or de-activating an electronic circuit, is able also to monitor the value of the pressure variation arising in the detection chamber 126, without, however, a current absorption in an inactive condition.

FIGS. 6A-6E show different possible shapes of the membrane 142 of the piezoelectric pressure sensor 130.

Figure 6A:
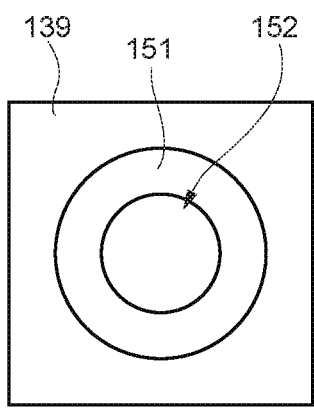
FIGS. 6A-6E are top views of possible embodiments of a piezoelectric sensor in the switch of FIGS. 4 and 5.

In FIG. 6A, in top view, the chip 139 has a square shape, the supporting layer 151 has a circular shape with a first diameter, and the piezoelectric stack 152 also has a circular shape, is concentric with, and has a smaller diameter than, the supporting layer 151.

Figure 6B:
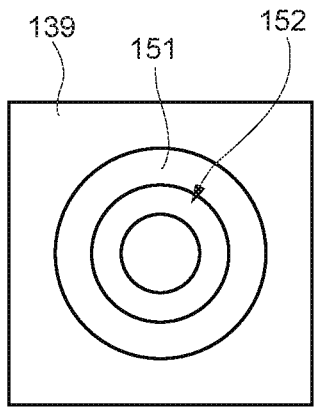

In FIG. 6B, the supporting layer 151 again has a circular shape with a first diameter, and the piezoelectric stack 152 has an annular shape, is concentric with, and has a maximum diameter smaller than the supporting layer 151.

Figure 6C:
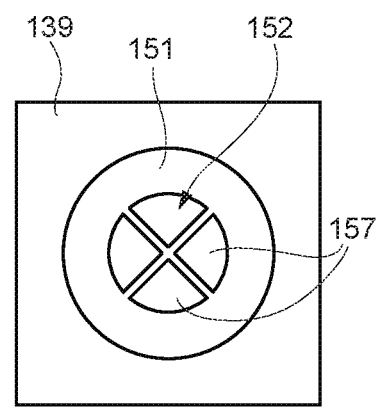

In FIG. 6C, the supporting layer 151 has again a circular shape with a first diameter and the piezoelectric stack 152 is formed by four circular sectors 157, arranged side-by-side, with a generally circular overall shape, with a smaller diameter than the supporting layer 151.

Figure 6D:
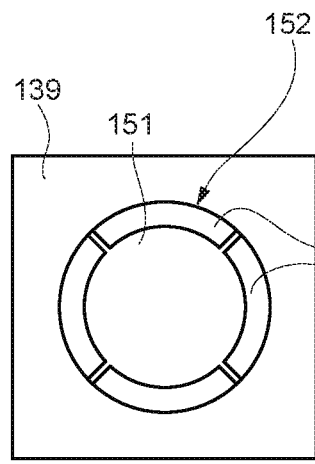

In FIG. 6D, the piezoelectric stack 152 is formed by four annular sectors 158, arranged side-by-side, so as to have a generally annular shape with a maximum diameter equal to the supporting layer 151.

Figure 6E:
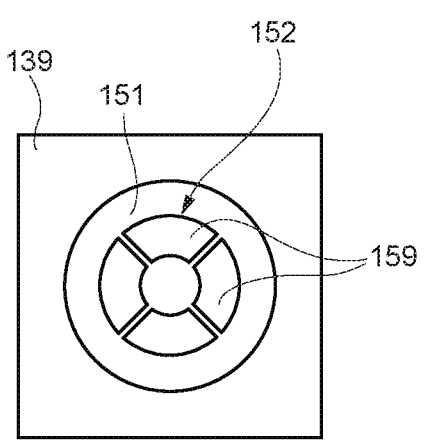

In FIG. 6E, the piezoelectric stack 152 is formed by four annular sectors 159, arranged side-by-side, so as to have a generally annular shape with a maximum diameter smaller than the supporting layer 151.

Figure 7:
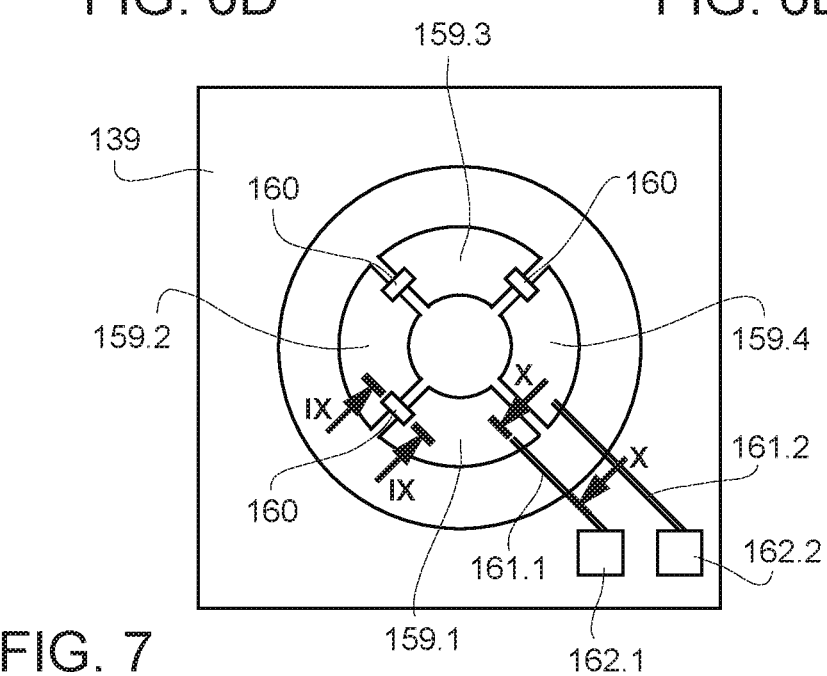
FIG. 7 shows in top view a possible connection of sensitive portions of the piezoelectric sensor of FIGS. 6C-6E.
Figure 8:
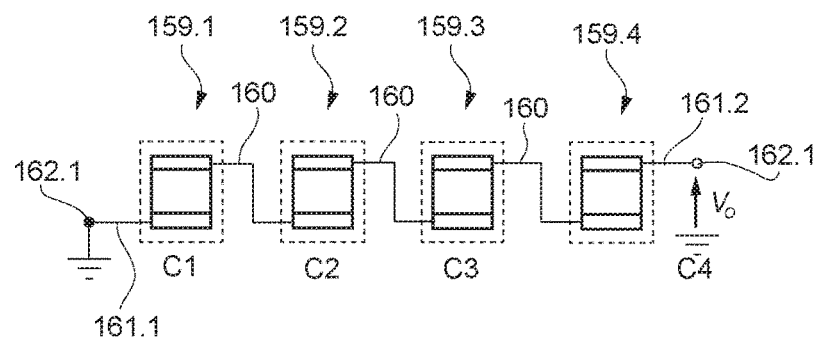
FIG. 8 is an electrical connection diagram for the piezoelectric sensor of FIGS. 6C-6E.
Figure 9:
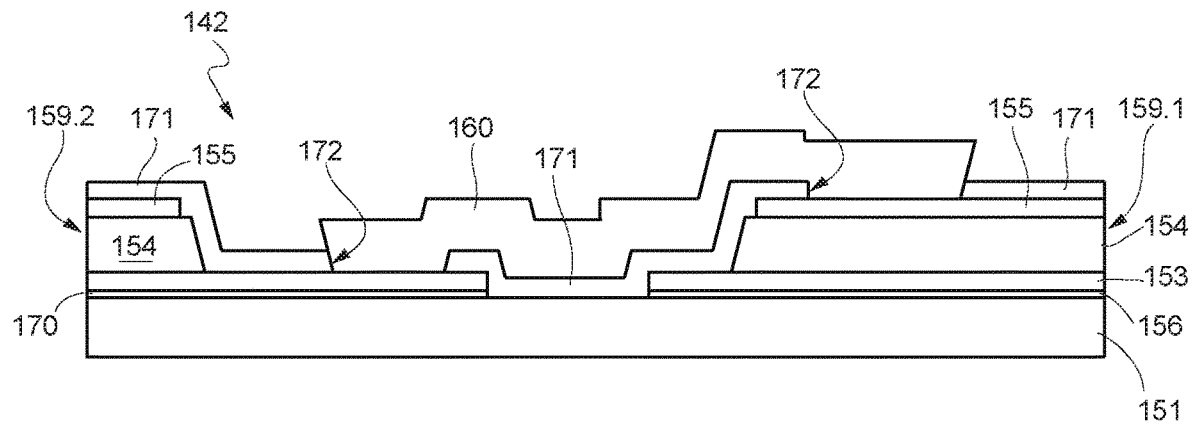
FIG. 9 is a cross-section taken along section line IX-IX of FIG. 7 of the piezoelectric sensor of FIGS. 6A-6C.

The circular sectors 157 and the annular sectors 159 of the differential pressure sensors 130 of FIGS. 6C-6E may be connected in series, as shown in FIGS. 7-9, purely by way of example, for the piezoelectric pressure sensor 130 of FIG. 6E.

In detail, in FIG. 7, the annular sectors 159 are referred to as first 159.1, second 159.2, third 159.3 and fourth 159.4 annular sectors, arranged side-by-side in the succession indicated by the respective number. Connection regions 160 extend between adjacent annular sectors, except for between the first 159.1 and the last 159. Four annular sectors, which are connected through a first and a second conductive region 161.1, 161.2 to a respective first and a respective second contact pad 162.1, 162.2.

The connection regions 160 between two adjacent annular sectors 159 are configured to electrically connect a bottom electrode region (153 in FIG. 3 or 4) of an annular sector 159.1, 159.2, 159.3 with a top electrode region 155 of an adjacent annular sector 159.2, 159.3, 159.4, as explained below with reference to FIG. 9. In this way, see also FIG. 8, the annular sectors 159.1-159.4, that may be electrically represented as capacitors C1-C4, are reciprocally connected in series between a first terminal (corresponding, for example, to the first contact pad 162.1), that is grounded, and a second terminal (corresponding, for example, to the second contact pad 162.2), outputting a voltage Vo related to the current generated by the piezoelectric pressure sensor 130 upon detection of a negative pressure, as explained above.

In this way, the best compromise between maximization of the total capacitance C and output voltage Vo is obtained.

FIG. 9 shows an embodiment of a connection region 160 between two adjacent annular sectors, for example, the first annular sector 159.1 and the second annular sector 159.2.

In FIG. 9, portions of the layers forming the stack 142 extend over the supporting layer 151. As may be noted, the portions of the core regions 156 and the portions of the bottom electrode regions 153, having the same shape, project from the respective portions of the piezoelectric region 154 and of the top electrode region 155, the passivation layer 171 extends over the entire surface of the membrane 142 and has openings 172 at the projecting portion of the bottom electrode region 153 of the second annular sector 159.2 and over the top electrode portion 155 of the first annular sector 159.1. A connection region 160 extends over the passivation layer 171 and in direct electrical contact with the bottom electrode region 153 of the second annular sector 159.2 and with the top electrode region 155 of the first annular sector 159.1 at the openings 172.

The connection region 160 is of conductive material, typically metal, for example TiW/Au.

Figure 10:
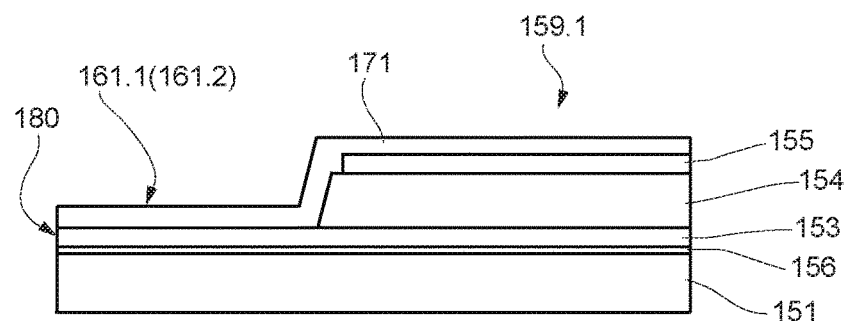
FIG. 10 is a cross-section taken along section line X-X of FIG. 7 of the piezoelectric sensor of FIGS. 6A-6C.

FIG. 10 shows an embodiment of the conductive regions 161.1, 161.2 (the figure regards in particular the first conductive region 161.1, but the structure of the second conductive region 161.2 is the same). In particular, the conductive regions 161.1, 161.2 are formed in the same layer of the bottom electrode region 153 (here identified as bottom electrode layer 180), as a continuation thereof. Moreover, also here the portions of the core region 156 extend underneath the conductive regions 161.1, 161.2, and the letter are covered by the passivation layer 171.

Finally, it is clear that modifications and variations may be made to the switch described and shown herein, without departing from the scope of the present disclosure, as defined in the attached claims. For instance, the various embodiments described may be combined so as to provide further solutions.

In addition, the shape of the sensitive portions of the piezoelectric pressure sensor may vary. Moreover, the circular sectors 157 and the annular sectors 159 of the differential pressure sensors 130 of FIGS. 6C-6E may also be in a number other than four.

The switch may be used in inhalation or air leakage detecting apparatus different from the described electronic cigarette.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A MEMS switch, actuatable by a fluid, comprising:
a piezoelectric pressure sensor;
a board having a face and a through hole, wherein the piezoelectric pressure sensor is fixed to the face of the board and includes:
a chip of semiconductor material having a through cavity overlying, and in fluid connection with, the through hole, and
a sensitive membrane extending over the through cavity and having a first and a second surface; and
a supporting wall configured to secure the board in an opening of a partition wall, which mutually separates a first and a second space from each other, with the first surface of the sensitive membrane facing the first space, and the second surface of the sensitive membrane facing the second space.

2. The MEMS switch according to claim 1, wherein the sensitive membrane comprises a piezoelectric stack including a bottom electrode region, a piezoelectric region and a top electrode region.

3. The MEMS switch according to claim 2, wherein the piezoelectric stack has a circular shape, an annular shape, a circular shape having a plurality of sectors, or an annular shape having a plurality of sectors.

4. The MEMS switch according to claim 2, wherein the piezoelectric stack includes a plurality of series-connected sectors that are adjacent and not contiguous with one another, with a top electrode portion of a first sector of the plurality of sectors electrically coupled to a bottom electrode portion of a second sector, adjacent to the first sector, a bottom electrode portion of the first sector and a top electrode portion of a last sector of the plurality of sectors being coupled to external terminals of the piezoelectric pressure sensor.

5. The MEMS switch according to claim 1, wherein the supporting wall has a tubular shape, surrounding the piezoelectric pressure sensor and having a first end and a second end, the first end of the supporting wall being bonded to the face of the board, and the second end of the supporting wall having retention means configured to be sealingly coupled to the partition wall.

6. The MEMS switch according to claim 5, wherein the retention means comprises a groove in the supporting wall and a seal gasket positioned within the groove.

7. The MEMS switch according to claim 1, further comprising a gel layer within a space defined by the supporting wall, the gel layer coating the piezoelectric pressure sensor and the face of the board.

8. The MEMS switch according to claim 1, further comprising a control unit bonded to the face of the board, the control unit electrically coupled to the piezoelectric pressure sensor and configured to detect a deformation of the sensitive membrane of the piezoelectric pressure sensor.

9. The MEMS switch according to claim 1, further comprising a barometric sensor bonded to the face of the board.

10. The MEMS switch according to claim 9, wherein the barometric sensor is a MEMS sensor including at least one of a capacitive sensor, a resistive sensor, or a strain gauge.

11. An apparatus, comprising:
a housing;
a wall dividing the housing into a first chamber and a second chamber; and
a MEMS switch, including:
a piezoelectric pressure sensor;
a board having a face and a through hole, wherein the piezoelectric pressure sensor is fixed to the face of the board and includes:
a chip of semiconductor material having a through cavity overlying, and in fluid connection with, the through hole, and
a sensitive membrane extending over the through cavity and having a first and a second surface; and
a supporting wall configured to secure the board in an opening of a partition wall, which mutually separates a first and a second space from each other, with the first surface of the sensitive membrane facing the first space, and the second surface of the sensitive membrane facing the second space,
wherein the apparatus is configured to detect a discontinuous passage of a fluid.

12. The apparatus according to claim 11, wherein the sensitive membrane comprises a piezoelectric stack including a bottom electrode region, a piezoelectric region and a top electrode region.

13. The apparatus according to claim 12, wherein the piezoelectric stack has a circular shape, an annular shape, a circular shape having a plurality of sectors, or an annular shape having a plurality of sectors.

14. The apparatus according to claim 11, wherein the supporting wall has a tubular shape, surrounding the piezoelectric pressure sensor and having a first end and a second end, the first end of the supporting wall being bonded to the face of the board, and the second end of the supporting wall configured to be sealingly coupled to the partition wall.

15. The apparatus according to claim 14, wherein the second end of the supporting wall includes a groove, and a seal gasket is positioned within the groove.

16. The apparatus according to claim 11, further comprising a gel layer within a space defined by the supporting wall, the gel layer coating the piezoelectric pressure sensor and the face of the board.

17. The apparatus according to claim 11, further comprising a control unit bonded to the face of the board, the control unit electrically coupled to the piezoelectric pressure sensor and configured to detect a deformation of the sensitive membrane of the piezoelectric pressure sensor.

18. An electronic cigarette, comprising:
a housing;
a wall dividing the housing into a first chamber and a second chamber; and a MEMS switch, including:
- a piezoelectric pressure sensor;
- a board having a face and a through hole, wherein the piezoelectric pressure sensor is fixed to the face of the board and includes:
  - a chip of semiconductor material having a through cavity overlying, and in fluid connection with, the through hole, and
  - a sensitive membrane extending over the through cavity and having a first and a second surface; and
- a supporting wall configured to secure the board in an opening of a partition wall, which mutually separates a first and a second space from each other, with the first surface of the sensitive membrane facing the first space, and the second surface of the sensitive membrane facing the second space.

19. The electronic cigarette according claim 18, further comprising a gel layer within a space defined by the supporting wall, the gel layer coating the piezoelectric pressure sensor and the face of the board.

20. The electronic cigarette according to claim 18, further comprising a control unit bonded to the face of the board, the control unit electrically coupled to the piezoelectric pressure sensor and configured to detect a deformation of the sensitive membrane of the piezoelectric pressure sensor.

* * * * *